(12) United States Patent
Millward et al.

(10) Patent No.: US 7,858,523 B2
(45) Date of Patent: *Dec. 28, 2010

(54) UNSYMMETRICAL LIGAND SOURCES, REDUCED SYMMETRY METAL-CONTAINING COMPOUNDS, AND SYSTEMS AND METHODS INCLUDING SAME

(75) Inventors: Dan Millward, Kuna, ID (US); Stefan Uhlenbrock, Boise, ID (US); Timothy A. Quick, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/500,738

(22) Filed: Jul. 10, 2009

(65) Prior Publication Data

US 2009/0275199 A1    Nov. 5, 2009

Related U.S. Application Data

(63) Continuation of application No. 11/169,082, filed on Jun. 28, 2005, now Pat. No. 7,572,731.

(51) Int. Cl.
H01L 21/44    (2006.01)
(52) U.S. Cl. .......... 438/681; 257/E21.17; 257/E21.271; 427/525
(58) Field of Classification Search ................. 438/681; 427/525; 534/15; 556/32, 34, 35
See application file for complete search history.

(56) References Cited

U.S. PATENT DOCUMENTS

| | | | |
|---|---|---|---|
| 5,256,244 A | 10/1993 | Ackerman | |
| 5,972,430 A | 10/1999 | DiMeo, Jr. et al. | |
| 6,225,237 B1 | 5/2001 | Vaartstra | |
| 6,455,717 B1 | 9/2002 | Vaartstra | |
| 6,682,602 B2 | 1/2004 | Vaartstra | |
| 6,828,256 B2 | 12/2004 | Vaartstra | |
| 6,939,578 B2 | 9/2005 | Bradley et al. | |
| 7,020,981 B2 | 4/2006 | Shero et al. | |

(Continued)

FOREIGN PATENT DOCUMENTS

DE    42 02 889 A1    8/1993

(Continued)

OTHER PUBLICATIONS

Ashton et al., "A Regioselective route to 3-Alkyl-1-aryl-1$H$-pyrazole-5-carboxylates: synthetic studies and structural assignments," *Journal of Heterocyclic Chemistry*, Mar. 1993;30(2):307-311.

(Continued)

*Primary Examiner*—Alexander G Ghyka
(74) *Attorney, Agent, or Firm*—Wells St. John P.S.

(57) ABSTRACT

The present invention provides metal-containing compounds that include at least one β-diketiminate ligand, and methods of making and using the same. In some embodiments, the metal-containing compounds are homoleptic complexes that include unsymmetrical β-diketiminate ligands. In other embodiments, the metal-containing compounds are heteroleptic complexes including at least one β-diketiminate ligand. The compounds can be used to deposit metal-containing layers using vapor deposition methods. Vapor deposition systems including the compounds are also provided. Sources for β-diketiminate ligands are also provided.

25 Claims, 1 Drawing Sheet

U.S. PATENT DOCUMENTS

| | | | |
|---|---|---|---|
| 7,416,994 | B2 | 8/2008 | Quick |
| 7,439,338 | B2 | 10/2008 | Millward et al. |
| 7,572,731 | B2 * | 8/2009 | Millward et al. ............ 438/681 |
| 2002/0187578 | A1 | 12/2002 | Hong |
| 2003/0113480 | A1 | 6/2003 | Kil et al. |
| 2004/0247905 | A1 | 12/2004 | Bradley et al. |
| 2005/0003075 | A1 | 1/2005 | Bradley et al. |
| 2005/0107283 | A1 | 5/2005 | Bradley et al. |
| 2005/0158479 | A1 | 7/2005 | Bradley et al. |
| 2005/0227007 | A1 | 10/2005 | Bradley et al. |
| 2006/0292303 | A1 | 12/2006 | Millward et al. |
| 2006/0292873 | A1 | 12/2006 | Millward et al. |
| 2007/0234962 | A1 | 10/2007 | Suzuki et al. |
| 2008/0214001 | A9 | 9/2008 | Millward et al. |
| 2008/0280455 | A1 | 11/2008 | Quick |
| 2009/0075488 | A1 | 3/2009 | Millward et al. |

FOREIGN PATENT DOCUMENTS

| | | |
|---|---|---|
| WO | WO 03/095701 | 11/2003 |
| WO | WO 2007/002672 | 1/2007 |
| WO | WO 2007/002673 | 1/2007 |
| WO | WO 2007/002674 | 1/2007 |

OTHER PUBLICATIONS

Barluenga et al., "Reaction of Fischer alkynylcarbene complexes with 1-azadiene derivatives: unexpected formation of 3, 4-dihydropyridines," *New Journal of Chemistry*, 2001; 25:8-10 (3 pgs). First published as an Advanced Article on the web Nov. 15, 2000.

Bourget-Merle et al., "The Chemistry of β-Diketiminatometal Complexes," *Chem. Rev.*, 2002;102:3031-3065. Published on Web Aug. 24, 2002.

Chisholm et al., "Lactide polymerization by well-defined calcium coordination complexes: comparisons with related magnesium and zinc chemistry," *Chem Commun. (Camb.)*, Jan. 7, 2003;1:48-49. First published as an Advance Article on the Web Dec. 5, 2002.

Clegg et al., "Alkaline Earth Diazapentadienyl Compounds: Structure of [Ba$_2${(C$_6$H$_{11}$)NC(Me)CHC(Me)-N(C$_6$H$_{11}$)}$_3${(SiMe$_3$)$_2$N}]," *Angew. Chem. Int. Ed*, 1998;37(6):796-797.

Coe et al., "Reactions of tetrafluoroethene oligomers. Part 9. Some reactions of perfluoro-(1-ethyl-1-methylpropyl)(s-butyl)ethanolide (an α-Lactone)," *Journal of the Chemical Society, Perkin Transactions I*, 1989;6:1097-1104.

Cui et al., "Synthesis and Structure of a Monomeric Aluminum(I) Compound [{HC(CMeNAr)$_2$}Al] (Ar=2,6-$i$Pr$_2$C$_6$H$_3$): A Stable Aluminum Analogue of a Carbene," *Agnew Chem. Int. Ed.*, 2000;39(23): 4274-4276.

Eisenstein et al., "Mono-, Di-, and Trianionic β-Diketiminato Ligands: A Computational Study and the Synthesis and Structure of [(YbL)$_3$(THF)], L= [{N(SiMe$_3$)C(Ph)}$_2$CH]," *J Am Chem Soc.*, 2003;125:10790-10791. Published on Web Aug. 15, 2003.

El-Kaderi et al., "Sandwich Complexes of the Heavier Alkaline Earth Metals Containing η$^5$-β-Diketiminato Ligand Sets," *Organometallics*, 2004;23: 4995-5002. Published on Web Sep. 14, 2004.

El-Kaderi et al., "Complexes of the heavier alkaline earth metals containing beta-diketiminato and iodide ligand sets," *Polyhedron*, Jan. 23, 2006;25(2):224-234.

El-Kaderi et al., "Synthesis, Structure, and Ligand Redistribution Equilibria of Mixed Ligand Complexes of the Heavier Group 2 Elements Containing Pyrazolato and β-Diketiminato Ligands," *Eur. J. Inorg. Chem.*, 2005:2081-2088. (published online Jun. 1, 2005).

England et al., "Reactions of amines with a dimer hexafluoropropene and with a perfluorovinyl sulfide prepared with hexafluoropropene," *Journal of Fluorine Chemistry*, 1981;28(2784):265-288.

Franceschini et al., "Volatile β-Ketoiminato- and β-Diketiminato-Based Zirconium Complexes as Potential MOCVD Precursors," *Inorganic Chemistry*, 2003;42(22):7273-7282. Published on Web Oct. 2, 2003.

Gusev et al., "Reaction of Methyldiacetylene with Primary Amines," *Bulletin of the Academy of Sciences of the USSR, Division Chemical Sciences (English Translation)*, 1974; 23:194-195 (2 pgs).

Harder, Sjoerd, "Homoleptic β-Diketiminato Complexes of the Alkaline-Earth Metals: Trends in the Series Mg, Ca, Sr, and Ba," *Organometallics*, 2002;21:3782-3787. Published on Web Aug. 9, 2002.

Harder, Sjoerd, "Intramolecular C-H Activation in Alkaline-Earth Metal Complexes," *Angew Chem Int Ed*, 2003;42:3430-3434.

Hardman et al., "Synthesis and characterization of the monomer Ga{(NDippCMe)$_2$CH} (Dipp=C$_6$H$_3$Pr$^i_2$-2,6): a low valent gallium(I) carbene analogue," *Chem. Comm.*, 2000:1991-1992. First published as an Advance Article on the Web Sep. 27, 2000.

Hawley G.G., "The Condensed Chemical Dictionary," *10th Edition*, 1981, Van Norstrand Reinhold Co., New York, 225-26.

Hill and Hitchcock, "Bis(Phosphinimino)methyl derivatives of Ca, Sr and Ba: facile access to heavier alkaline earth organometallic chemistry," *Chem Commun. (Camb.)*, 2003;14:1758-1759. First published as an Advance Article on the Web Jun. 18, 2003.

Hitchcock et al., "New reactions of β-diketiminatolanthanoid complexes: sterically induced self-deprotonation of β-diketiminato ligands," *Chem Commun.*, 2005:951-953. First Published as an Advance Article on the Web Jan. 6, 2005.

Hitchcock et al., "Synthesis, structure and reductive dechlorination of the C-centred phosphorus (III) β-diketiminate Pcl(Ph)L [L=C{C(Me)NC$_6$H$_3$Pr$^i_2$-2,6} {C(Me)NHC$_6$H$_3$Pr$^i_2$-2,6}]," *Chem Commun.*, 2003;1142-1143. (Published Electronically Apr. 16, 2003).

Holland et al., "Electronically Unsaturated Three-Coordinate Chloride and Methyl Complexes of Iron, Cobalt, and Nickel," *J Am. Chem. Soc.*, 2002;124:14416-14424. Published on the Web Nov. 8, 2002.

Knorr et al., "Configurational stability and reduced $^1$H-NMR shifts of (pseudo)tetrahedral nickel(II) bis-chelates of 1,3-diimines [1]," English language translation (19 pgs) of *Chem. Ber.*, 1981; 114:2104-2115 in German (12 pgs).

Li et al., "Synthesis and Characterization of Copper(I) Amidinates as Precursors for Atomic Layer Deposition (ALD) of Copper Metal," *Inorganic Chemistry*, 2005;44: 1728-1735. Published on the Web Feb. 3, 2005.

Park et al., "Routes to N, N'— Unsymmetrically Substituted 1, 3-Diketimines," *Journal of Organic Chemistry*, 2005; 70:2075-2081 (7 pgs). Published on Web Feb. 9, 2005.

Piers and Emslie, "Non-cyclopentadienyl ancillaries in organogroup 3 metal chemistry: a fine balance in ligand design," *Coordination Chemistry Reviews*, 2002;233-234:131-155.

Rische et al., "New Tungsten(VI) Guanidinato Complexes: Synthesis, Characterization, and Application in Metal-Organic Chemical Vapor Depostion of Tungsten Nitride Thin Films," *Chem. Mater.*, 2006; 18:6075-6082 (8 pgs). Published on the web Nov. 15, 2006.

Schroth et al., "Nucleophilic addition of amines to diacetylene and 1 amniobut-1-en-3-ine," English language translation (4 pgs) of *Z. Chem.*, 1969; 9(3):110-111 (2 pgs).

Shimokawa and Itoh, "The First β-Diketiminate-Ag(I) Complexes. Macrocyclic Dinuclear and Tetranuclear Ag(I)- Complexes and Linear Coordination Polymer Ag(I)-Complex," *Inorganic Chemistry*, 2005;44: 3010-3012. Published on the Web Apr. 5, 2005.

Vehkamäki et al., "Growth of SrTiO$_3$ and BaTO$_3$ Thin Films by Atomic Layer Deposition," *Electrochemical and Solid-State Letters*, 1999;2(10): 504-506. Available electronically Aug. 5, 1999.

Yakimovich et al., "Tautomerism in the series of products from the condensation of beta-ketoaldehydes with N,N-disubstituted hydrazines," *Journal of Organic Chemistry of the USSR*, 1990;26(12):2174-2181.

* cited by examiner

UNSYMMETRICAL LIGAND SOURCES, REDUCED SYMMETRY METAL-CONTAINING COMPOUNDS, AND SYSTEMS AND METHODS INCLUDING SAME

This is a continuation of application Ser. No. 11/169,082, filed Jun. 28, 2005, (pending), which is incorporated herein by reference.

BACKGROUND

The scaling down of integrated circuit devices has created a need to incorporate high dielectric constant materials into capacitors and gates. The search for new high dielectric constant materials and processes is becoming more important as the minimum size for current technology is practically constrained by the use of standard dielectric materials. Dielectric materials containing alkaline earth metals can provide a significant advantage in capacitance compared to conventional dielectric materials. For example, the perovskite material $SrTiO_3$ has a disclosed bulk dielectric constant of up to 500.

Unfortunately, the successful integration of alkaline earth metals into vapor deposition processes has proven to be difficult. For example, although atomic layer deposition (ALD) of alkaline earth metal diketonates has been disclosed, these metal diketonates have low volatility, which typically requires that they be dissolved in organic solvent for use in a liquid injection system. In addition to low volatility, these metal diketonates generally have poor reactivity, often requiring high substrate temperatures and strong oxidizers to grow a film, which is often contaminated with carbon. Other alkaline earth metal sources, such as those including substituted or unsubstituted cyclopentadienyl ligands, typically have poor volatility as well as low thermal stability, leading to undesirable pyrolysis on the substrate surface.

New sources and methods of incorporating high dielectric materials are being sought for new generations of integrated circuit devices.

SUMMARY OF THE INVENTION

The present invention provides metal-containing compounds (i.e., metal-containing complexes) that include at least one β-diketiminate ligand, and methods of making and using, and vapor deposition systems including the same. The presently disclosed metal-containing compounds have reduced symmetry compared to known homoleptic complexes with symmetrical ligands. The reduced symmetry may result from the unsymmetric ligands themselves, the coordination of different types of ligands, or both. Reduced symmetry may lead to desirable properties (e.g., one or more of higher vapor pressure, lower melting point, and lower sublimation point) for use in vapor deposition methods.

In one aspect, the present invention provides a method of forming a metal-containing layer on a substrate (e.g. a semiconductor substrate or substrate assembly) using a vapor deposition process. The method can be useful in the manufacture of semiconductor structures. The method includes: providing a substrate; providing a vapor including at least one compound of the formula (Formula I):

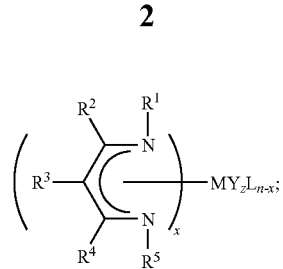

and contacting the vapor including the at least one compound of Formula I with the substrate (and typically directing the vapor to the substrate) to form a metal-containing layer on at least one surface of the substrate. The reduced symmetry compound of the formula (Formula I) includes at least one unsymmetrical β-diketiminate ligand, wherein M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; x is from 1 to n; and each $R^1$, $R^2$, $R^3$, $R^4$, and $R^5$ is independently hydrogen or an organic group; with the proviso that one or more of the following apply: $R^1$ is different than $R^5$, or $R^2$ is different than $R^4$.

In another aspect, the present invention provides a method of forming a metal-containing layer on a substrate (e.g. a semiconductor substrate or substrate assembly) using a vapor deposition process. The method can be useful in the manufacture of semiconductor structures. The method includes: providing a substrate; providing a vapor including at least one compound of the formula (Formula II):

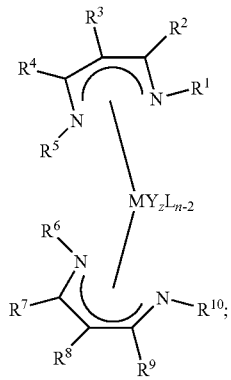

and contacting the vapor including the at least one compound of Formula II with the substrate (and typically directing the vapor to the substrate) to form a metal-containing layer on at least one surface of the substrate. The reduced symmetry compound of the formula (Formula II) includes two different symmetrical β-diketiminate ligands, wherein: M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; each $R^1$, $R^2$, $R^3$, $R^4$, $R^5$, $R^6$, $R^7$, $R^8$, $R^9$, and $R^{10}$ is independently hydrogen or an organic group; and $R^1=R^5$, $R^2=R^4$, $R^6=R^{10}$ and $R^7=R^9$.

In another aspect, the present invention provides metal-containing compounds having at least one unsymmetrical β-diketiminate ligand, precursor compositions including such compounds, vapor deposition systems including such compounds and methods of making such compounds. Such metal-containing compounds include those of the formula (Formula I):

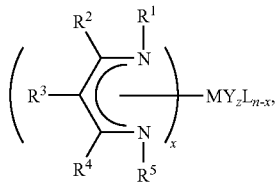

wherein: M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; and x is from 1 to n; and each $R^1$, $R^2$, $R^3$, $R^4$, and $R^5$ is independently hydrogen or an organic group; with the proviso that one or more of the following apply: $R^1$ is different than $R^5$, or $R^2$ is different than $R^4$. The present invention also provides sources for unsymmetrical β-diketiminate ligands, and methods of making same, which are useful for making metal-containing compounds having at least one unsymmetrical β-diketiminate ligand.

In another aspect, the present invention provides metal-containing compounds having two different symmetrical β-diketiminate ligands, precursor compositions including such compounds, vapor deposition systems including such compounds, and methods of making such compounds. Such metal-containing compounds include those of the formula (Formula II):

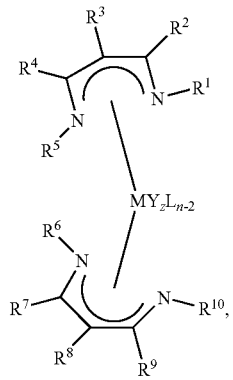

wherein: M is selected from the group consisting of a Group 2 metal: a Group 3 metal, a Lanthanide, and combinations thereof; each L is independently an anionic ligand; each Y is independently a neutral ligand; n represents the valence state of the metal; z is from 0 to 10; each $R^1$, $R^2$, $R^3$, $R^4$, $R^5$, $R^6$, $R^7$, $R^8$, $R^9$, and $R^{10}$ is independently hydrogen or an organic group; and $R^1{=}\!\!\!\!/\, R^5$, $R^2{=}\!\!\!\!/\, R^4$, $R^6{=}\!\!\!\!/\, R^{10}$, and $R^7{=}\!\!\!\!/\, R^9$.

Advantageously, the reduced symmetry metal-containing compounds of the present invention include elements of asymmetry that may lead to desirable properties (e.g., one or more of higher vapor pressure, lower melting point, and lower sublimation point) for use in vapor deposition methods.

DEFINITIONS

As used herein, formulas of the type:

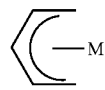

are used to represent pentadienyl-group type ligands (e.g., β-diketiminate ligands) having delocalized electron density that are coordinated to a metal. The ligands may be coordinated to the metal through one, two, three, four, and/or five atoms (i.e., $\eta^1$-, $\eta^2$-, $\eta^3$-, $\eta^4$-, and/or $\eta^5$-coordination modes).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for metal-containing compounds of this invention are those that do not interfere with the formation of a metal oxide layer using vapor deposition techniques. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e. carbon-carbon double bonds), such as a vinyl group. The term "alkynyl group" means an unsaturated, linear or branched monovalent hydrocarbon group with one or more carbon-car-bon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitro-en, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

As used herein, "metal-containing" is used to refer to a material, typically a compound or a layer, that may consist entirely of a metal, or may include other elements in addition to a metal. Typical metal-containing compounds include, but are not limited to, metals, metal-ligand complexes, metal salts, organometallic compounds, and combinations thereof.

Typical metal-containing layers include, but are not limited to, metals, metal oxides, metal silicates, and combinations thereof.

As used herein, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

The terms "deposition process" and "vapor deposition process" as used herein refer to a process in which a metal-containing layer is formed on one or more surfaces of a substrate (e.g., a doped polysilicon wafer) from vaporized precursor composition(s) including one or more metal-containing compounds. Specifically, one or more metal-containing compounds are vaporized and directed to and/or contacted with one or more surfaces of a substrate (e.g., semiconductor substrate or substrate assembly) placed in a deposition chamber. Typically, the substrate is heated. These metal-containing compounds form (e.g., by reacting or decomposing) a non-volatile, thin, uniform, metal-containing layer on the surface(s) of the substrate. For the purposes of this invention, the term "vapor deposition process" is meant to include both chemical vapor deposition processes (including pulsed chemical vapor deposition processes) and atomic layer deposition processes.

"Chemical vapor deposition" (CVD) as used herein refers to a vapor deposition process wherein the desired layer is deposited on the substrate from vaporized metal-containing compounds (and any reaction gases used) within a deposition chamber with no effort made to separate the reaction components. In contrast to a "simple" CVD process that involves the substantial simultaneous use of the precursor compositions and any reaction gases, "pulsed" CVD alternately pulses these materials into the deposition chamber, but does not rigorously avoid intermixing of the precursor and reaction gas streams, as is typically done in atomic layer deposition or ALD (discussed in greater detail below).

The term "atomic layer deposition" (ALD) as used herein refers to a vapor deposition process in which deposition cycles, preferably a plurality of consecutive deposition cycles, are conducted in a process chamber (i.e., a deposition chamber). Typically, during each cycle the precursor is chemisorbed to a deposition surface (e.g., a substrate assembly surface or a previously deposited underlying surface such as material from a previous ALD cycle), forming a monolayer or sub-monolayer that does not readily react with additional precursor (i.e., a self-limiting reaction). Thereafter, if necessary, a reactant (e.g., another precursor or reaction gas) may subsequently be introduced into the process chamber for use in converting the chemisorbed precursor to the desired material on the deposition surface. Typically, this reactant is capable of further reaction with the precursor. Further, purging steps may also be utilized during each cycle to remove excess precursor from the process chamber and/or remove excess reactant and/or reaction byproducts from the process chamber after conversion of the chemisorbed precursor. Further, the term "atomic layer deposition," as used herein, is also meant to include processes designated by related terms such as, "chemical vapor atomic layer deposition", "atomic layer epitaxy" (ALE) (see U.S. Pat. No. 5,256,244 to Ackerman), molecular beam epitaxy (MBE), gas source MBE, or organo-metallic MBE, and chemical beam epitaxy when performed with alternating pulses of precursor composition(s), reactive gas, and purge (e.g., inert carrier) gas.

As compared to the one cycle chemical vapor deposition (CVD) process, the longer duration multi-cycle ALD process allows for improved control of layer thickness and composition by self-limiting layer growth, and minimizing detrimental gas phase reactions by separation of the reaction components. The self-limiting nature of ALD provides a method of depositing a film on a wide variety of reactive surfaces, including surfaces with irregular topographies, with better step coverage than is available with CVD or other "line of sight" deposition methods such as evaporation or physical vapor deposition (PVD or sputtering).

DETAILED DESCRIPTION OF CERTAIN EMBODIMENTS

Figure 1:
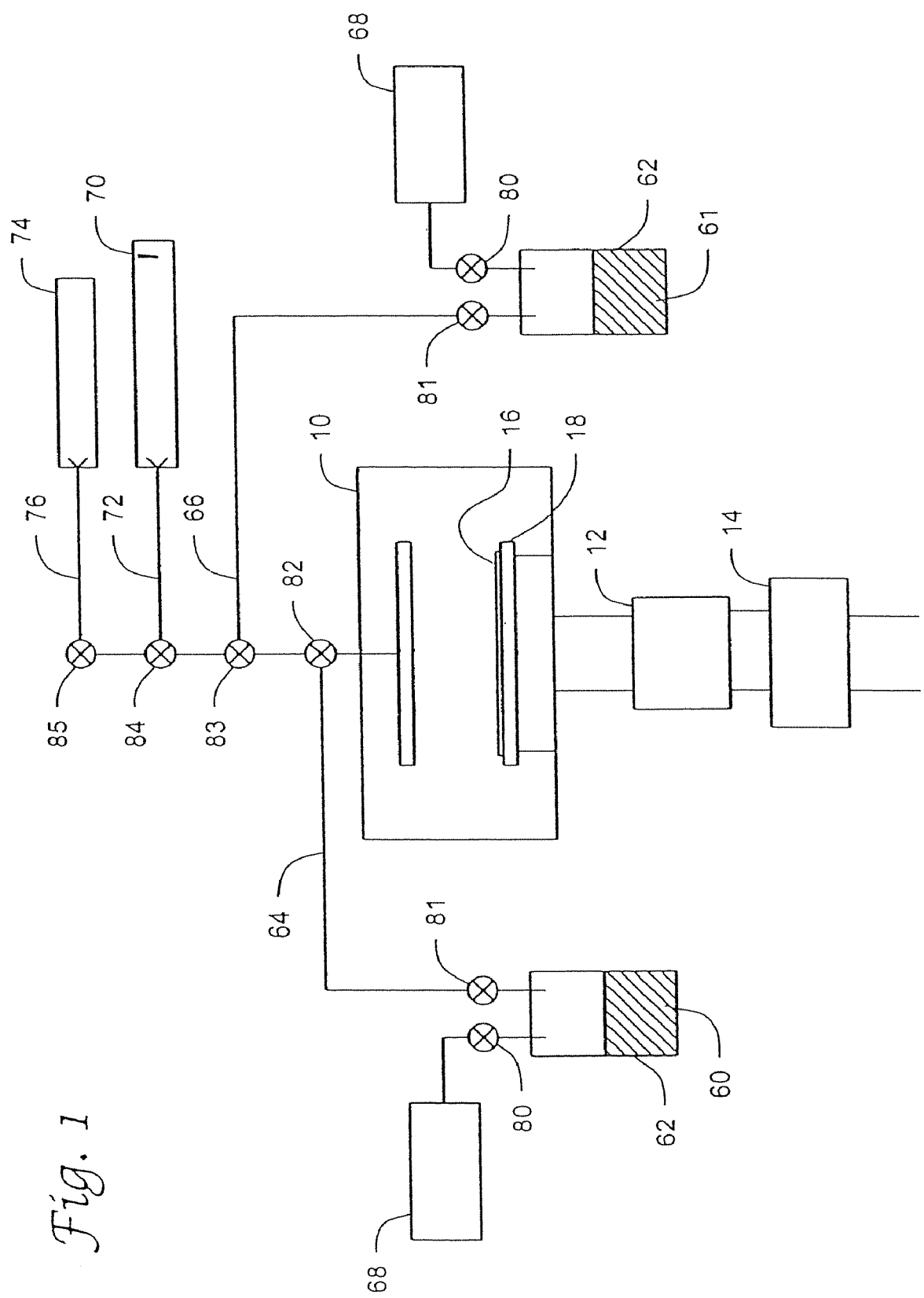
FIG. 1 is a perspective view of a vapor deposition system suitable for use in methods of the present invention.

The present invention provides metal-containing compounds (i.e., metal-containing complexes) that include at least one β-diketiminate ligand, and methods of making and using, and vapor deposition systems including the same. In some embodiments, the at least one β-diketiminate ligand can be in the $\eta^5$-coordination mode. In some embodiments, the metal-containing compounds are homoleptic complexes (i.e., complexes in which the metal is bound to only one type of ligand) that include unsymmetrical β-diketiminate ligands. In other embodiments, the metal-containing compounds are heteroleptic complexes (i.e., complexes in which the metal is bound to more than one type of ligand) including at least one β-diketiminate ligand, which can be symmetric or unsymmetric. Thus, the presently disclosed metal-containing compounds have reduced symmetry compared to known homoleptic complexes with symmetrical ligands. The reduced symmetry may result from the unsymmetric ligands themselves, the coordination of different types of ligands, or both. Reduced symmetry may lead to desirable properties (e.g., one or more of higher vapor pressure, lower melting point, and lower sublimation point) for use in vapor deposition methods.

Compounds with at Least One Unsymmetrical Ligand

In one embodiment, metal-containing compounds including at least one unsymmetrical β-diketiminate ligand, and precursor compositions including such compounds, are disclosed. Such compounds include a compound of the formula (Formula I):

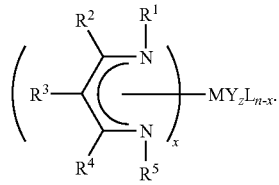

M is a Group 2 metal (e.g., Ca, Sr, Ba), a Group 3 metal (e.g., Sc, Y, La), a Lanthanide (e.g., Pr, Nd), or a combination thereof. Preferably M is Ca, Sir, or Ba. Each L is independently an anionic ligand; each Y is independently a neutral ligand; n represents the valence state of the metal; z is from 0 to 10; and x is from 1 to n.

Each $R^1$, $R^2$, $R^3$, $R^4$, and $R^5$ is independently hydrogen or an organic group (e.g., an alkyl group, and preferably, for example, an alkyl moiety); with the proviso that one or more of the following apply: $R^1$ is different than $R^5$, or $R^2$ is different than $R^4$. In certain embodiments, $R^1$, $R^2$, $R^3$, $R^4$, and $R^5$ are each independently hydrogen or an organic group having 1 to 10 carbon atoms (e.g., methyl, ethyl, propyl, isopropyl, butyl, sec-butyl, tert-butyl). In certain embodiments, $R^1$=isopropyl and $R^5$=tert-butyl. In certain embodiments, $R^2$ and/or $R^4$ are methyl. In certain embodiments, $R^3$ is H. Such an exemplary compound of Formula I is the compound in which $R^2$=$R^4$=methyl, $R^3$=H, $R^1$=isopropyl, and $R^5$=tert-butyl.

L can represent a wide variety of anionic ligands. Exemplary anionic ligands (L) include halides, alkoxide groups, amide groups, mercaptide groups, cyanide, alkyl groups, amidinate groups, guanidinate groups, isoureate groups, β-diketonate groups, β-iminoketonate groups, β-diketiminate groups, and combinations thereof. In certain embodiments, L is a β-diketiminate group having a structure that is the same as that of the β-diketiminate ligand shown in Formula I. In other certain embodiments, L is a β-diketiminate group (e.g., symmetric or unsymmetric) having a structure that is different than that of the β-diketiminate ligand shown in Formula I.

Y represents an optional neutral ligand. Exemplary neutral ligands (Y) include carbonyl (CO), nitrosyl (NO), ammonia ($NH_3$), amines ($NR_3$), nitrogen ($N_2$), phosphines ($PR_3$), alcohols (ROH), water ($H_2O$), tetrahydrofuran, and combinations thereof, wherein each R independently represents hydrogen or an organic group. The number of optional neutral ligands (Y) is represented by z, which is from 0 to 10, and preferably from 0 to 3. More preferably, Y is not present (i.e., z=0).

In one embodiment, a metal-containing compound including at least one unsymmetrical β-diketiminate ligand can be made, for example, by a method that includes combining components including an unsymmetrical β-diketiminate ligand source, a metal source, optionally a source for a neutral ligand Y, and a source for an anionic ligand L, which can be the same or different than the unsymmetrical β-diketiminate ligand source. Typically, a ligand source can be deprotonated to become a ligand.

An exemplary method includes combining components including: a ligand source of the formula (Formula III):

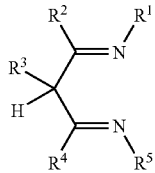

or a tautomer thereof;

a source for an anionic ligand L (e.g., as described herein); optionally a source for a neutral ligand Y (e.g., as described herein); and a metal (M) source under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

The metal (M) source can be selected from the group consisting of a Group II metal source, a Group III metal source, a Lanthanide metal source, and combinations thereof. Exemplary metal sources include, for example, a M(II) bis(hexamethyldisilazane), a M(II) bis(hexamethyldisilazane) bis(tetrahydrofuran), or combinations thereof.

Each $R^1$, $R^2$, $R^3$, $R^4$, and $R^5$ is independently hydrogen or an organic group (e.g., an alkyl group, and preferably, for example, an alkyl moiety), with the proviso that one or more of the following apply: $R^1$ is different than $R^5$, or $R^2$ is different than $R^4$.

The method provides a metal-containing compound of the formula (Formula I):

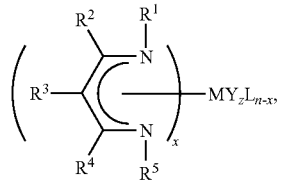

wherein M, L, Y, $R^1$, $R^2$, $R^3$, $R^4$, and $R^5$ are as defined above, n represents the valence state of the metal, z is from 0 to 10, and x is from 1 to n.

Unsymmetrical β-diketiminate ligand sources can be made, for example, using condensation reactions. For example, exemplary unsymmetrical β-diketiminate ligand sources can be made by a method including combining components including an amine of the formula $R^1NH_2$; a compound of the formula (Formula V):

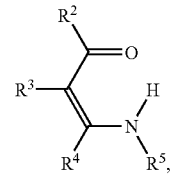

or a tautomer thereof; and an agent capable of activating the carbonyl group for reaction with the amine, under conditions sufficient to provide a ligand source of the formula (Formula III):

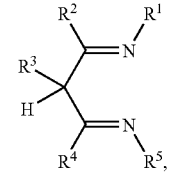

or a tautomer thereof.

Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

Each $R^1$, $R^2$, $R^3$, $R^4$, and $R^5$ is independently hydrogen or an alkyl moiety having 1 to 10 carbon atoms (e.g., methyl, ethyl, propyl, isopropyl, butyl, sec-butyl, tert-butyl), with the proviso that one or more of the following apply: $R^1$ is different than $R^5$, or $R^2$ is different than $R^4$. Accordingly, the present invention also provides ligand sources of Formula III. In certain embodiments, $R^1$=isopropyl and $R^5$=tert-butyl. In certain embodiments, $R^2$ and/or $R^4$ are methyl. In certain embodiments, $R^3$ is H. Such an exemplary compound of Formula III is the compound in which $R^2=R^4$=methyl, $R^3$=H, $R^1$=isopropyl, and $R^5$=tert-butyl.

Tautomers of compounds of Formula III and Formula V include isomers in which a hydrogen atom is bonded to another atom. Typically, tautomers can be in equilibrium with one another.

Specifically, the present invention contemplates tautomers of Formula III including, for example,

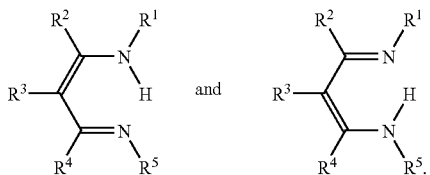

Similarly, the present invention contemplates tautomers of Formula V including, for example,

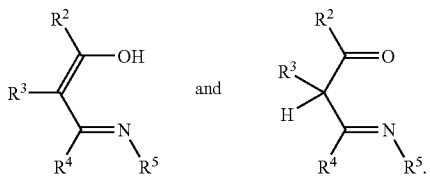

Suitable agents capable of activating a carbonyl group for reaction with an amine are well known to those of skill in the art and include, for example, alkylating agents. Exemplary alkylating agents include triethyloxonium tetrafluoroborate, dimethyl sulfate, nitrosoureas, mustard gases (e.g., 1,1-thiobis(2-chloroethane)), and combinations thereof.

Additional metal-containing compounds including at least one unsymmetrical β-diketiminate ligand can be made, for example, by ligand exchange reactions between a metal-containing compound including at least one unsymmetrical β-diketiminate ligand and a metal-containing compound including at least one different β-diketiminate ligand. Such an exemplary method includes combining components including a compound of the formula (Formula I):

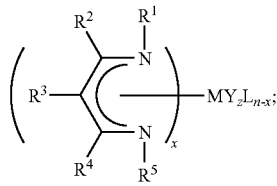

and a compound of the formula (Formula VI):

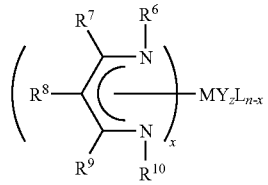

under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

Each M is a Group 2 metal, a Group 3 metal, a Lanthanide, or a combination thereof; each L is independently an anionic ligand; each Y is independently a neutral ligand; n represents the valence state of the metal; z is from 0 to 10; and x is from 1 to n.

Each $R^1$, $R^2$, $R^3$, $R^4$, $R^5$, $R^6$, $R^7$, $R^8$, $R^9$, and $R^{10}$ is independently hydrogen or an organic group; and the β-diketiminate ligands shown in Formula I and Formula VI have different structures, with the proviso that one or more of the following apply: $R^1$ is different than $R^5$, $R^2$ is different than $R^4$, $R^6$ is different than $R^{10}$, or $R^7$ is different than $R^9$.

The method can provide a metal-containing compound of the formula (Formula II):

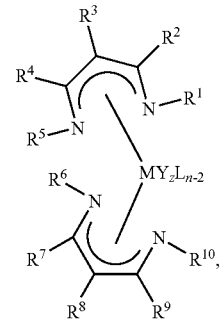

wherein M, L, Y, $R^1$, $R^2$, $R^3$, $R^4$, $R^5$, $R^6$, $R^7$, $R^8$, $R^9$, $R^{10}$, n, and z are as defined above, and the two β-diketiminate ligands shown in Formula II have different structures.

Heteroleptic Compounds with Different Symmetrical Ligands

In another embodiment, compounds that are heteroleptic metal-containing compounds including different symmetrical β-diketiminate ligands, and precursor compositions including such compounds, are disclosed. Such compounds include a compound of the formula (Formula II):

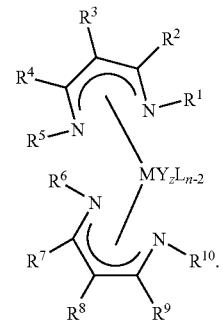

M is a Group 2 metal (e.g., Ca, Sr, Ba), a Group 3 metal (e.g., Sc, Y. La), a Lanthanide (e.g., Pr, Nd), or combinations thereof. Preferably M is Ca, Sr, or Ba. Each L is independently an anionic ligand; each Y is independently a neutral ligand; n represents the valence state of the metal; and z is from 0 to 10.

Each $R^1$, $R^2$, $R^3$, $R^4$, $R^5$, $R^6$, $R^7$, $R^8$, $R^9$, and $R^{10}$ is independently hydrogen or an organic group (e.g., an alkyl group, and preferably, for example, an alkyl moiety); $R^1=R^5$, $R^2=R^4$, $R^6=R^{10}$, and $R^7=R^9$; and the two β-diketiminate ligands shown in Formula II have different structures. In certain embodimnent, each $R^1$, $R^2$, $R^3$, $R^4$, $R^5$, $R^6$, $R^7$, $R^8$, $R^9$, and $R^{10}$ is independently hydrogen or an organic group having 1 to 10 carbon atoms (e.g., methyl, ethyl, propyl, isopropyl, butyl, sec-butyl, tert-butyl). In certain embodiments, $R^1=R^5$=tert-butyl, and $R^6=R^{10}$=isopropyl. In certain embodiments, $R^2$, $R^4$, $R^7$, and/or $R^9$ are methyl. In certain embodiments, $R^3$ and/or $R^8$ are H. Such an exemplary compound of Formula II is the compound in which $R^2=R^4=R^7=R^9$=methyl, $R^3=R^8$=H, $R^1=R^5$=tert-butyl, and $R^6=R^{10}$=isopropyl.

L represents a wide variety of optional anionic ligands. Exemplary anionic ligands (L) include halides, alkoxide groups, amide groups, mercaptide groups, cyanide, alkyl groups, amidinate groups, guanidinate groups, isoureate groups, β-diketonate groups, β-iminoketonate groups, β-diketiminate groups, and combinations thereof. In certain embodiments, L is a β-diketiminate group having a structure that is the same as that of one of the β-diketiminate ligands shown in Formula II. In other certain embodiments. L is a β-diketiminate group (e.g. symmetric or unsymmetric) having a structure that is different than either of the β-diketiminate ligands shown in Formula II.

Y represents an optional neutral ligand. Exemplary neutral ligands (Y) include carbonyl (CO), nitrosyl (NO), ammonia ($NH_3$), amines ($NR_3$), nitrogen ($N_2$), phosphines ($PR_3$), alcohols (ROH), water ($H_2O$), tetrahydrofuran, and combinations thereof, wherein each R independently represents hydrogen or an organic group. The number of optional neutral ligands (Y) is represented by z, which is from 0 to 10, and preferably from 0 to 3. More preferably, Y is not present (i.e. z=0).

In one embodiment, a metal-containing compound including different symmetrical β-diketiminate ligands can be made, for example, by a method that includes combining components including at least two different symmetrical β-diketiminate ligand sources and a metal source. Symmetrical β-diketiminate ligand sources can be made as described, for example, in El-Kaderi et al., *Organometallics,* 23:4995-5002 (2004).

An exemplary method includes combining components including: a ligand source of the formula (Formula III):

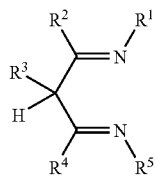

or a tautomer thereof;

a ligand source of the formula (Formula IV):

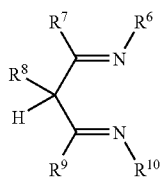

or a tautomer thereof; and optionally a source for an anionic ligand L (e.g., as described herein); optionally a source for a neutral ligand Y (e.g., as described herein); and a metal (M) source under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

The metal (M) source is a Group II metal source, a Group III metal source, a Lanthanide metal source, or a combination thereof. Exemplary metal sources include, for example, a M(II) bis(hexamethyldisilazane), a M(II) bis(hexamethyldisilazane)bis(tetrahydrofuran), or combinations thereof.

Each $R^1$, $R^2$, $R^3$, $R^4$, $R^5$, $R^6$, $R^7$, $R^8$, $R^9$, and $R^{10}$ is independently hydrogen or an organic group (e.g., an alkyl group, and preferably, for example, an alkyl moiety); $R^1=R^5$, $R^2=R^4$, $R^6=R^{10}$, and $R^7=R^9$, and the ligand sources shown in Formula III and Formula IV have different structures.

The method can provide a metal-containing compound of the formula (Formula II):

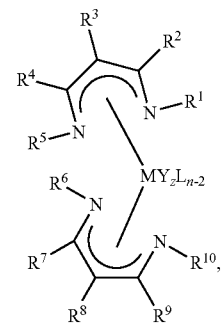

wherein M, L, Y, $R^1$, $R^2$, $R^3$, $R^4$, $R^5$, $R^6$, $R^7$, $R^8$, $R^9$, and $R^{10}$ are as defined above, n represents the valence of the metal, and z is from 0 to 10.

Specifically, the present invention contemplates tautomers of Formula IV including, for example,

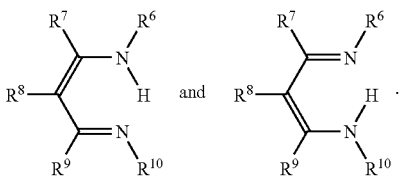

In another embodiment, a metal-containing compound including different symmetrical β-diketiminate ligands can be made, for example, by ligand exchange reactions between metal-containing compounds including different symmetrical β-diketiminate ligands. Such an exemplary method includes combining components including a compound of the formula (Formula I):

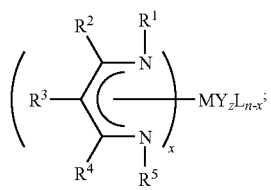

and a compound of the formula (Formula VI):

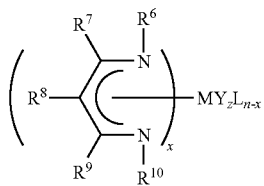

under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

Each M is a Group 2 metal, a Group 3 metal, a Lanthanide, or a combination thereof; each L is independently an anionic ligand; each Y is independently a neutral ligand; n represents the valence state of the metal; z is from 0 to 10; and x is from 1 to n.

Each $R^1$, $R^2$, $R^3$, $R^4$, $R^5$, $R^6$, $R^7$, $R^8$, $R^9$, and $R^{10}$ is independently hydrogen or an organic group; $R^1=R^5$, $R^2=R^4$, $R^6=R^{10}$, and $R^7=R^9$; and the β-diketiminate ligands shown in Formula I and Formula VI have different structures.

The method can provide a metal-containing compound of the formula (Formula II):

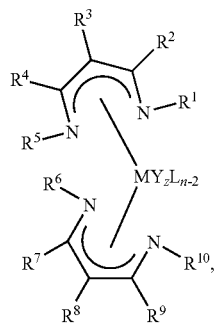

wherein M, L, Y, $R^1$, $R^2$, $R^3$, $R^4$, $R^5$, $R^6$, $R^7$, $R^8$, $R^9$, $R^{10}$, n, and z are as defined above.

Other Metal-Containing Compounds

Precursor compositions that include a metal-containing compound that includes at least one β-diketiminate ligand can be useful for depositing metal-containing layers using vapor deposition methods. In addition, such vapor deposition methods can also include precursor compositions that include one or more different metal-containing compounds. Such precursor compositions can be deposited/chemisorbed, for example in an ALD process discussed more fully below, substantially simultaneously with or sequentially to, the precursor compositions including metal-containing compounds with at least one β-diketiminate ligand. The metals of such different metal-containing compounds can include, for example, Ti, Ta, Bi, Hf. Zr, Pb, Nb, Mg, Al, and combinations thereof. Suitable different metal-containing compounds include, for example, tetrakis titanium isopropoxide, titanium tetrachloride, trichlorotitanium dialkylamides, tetrakis titanium dialkylamides, tetrakis hafnium dialkylamides, trimethyl aluminum, zirconium (IV) chloride, pentakis tantalum ethoxide, and combinations thereof.

Vapor Deposition Methods

The metal-containing layer can be deposited, for example, on a substrate (e.g., a semiconductor substrate or substrate assembly). "Semiconductor substrate" or "substrate assembly" as used herein refer to a semiconductor substrate such as a base semiconductor layer or a semiconductor substrate having one or more layers, structures, or regions formed thereon A base semiconductor layer is typically the lowest layer of silicon material on a wafer or a silicon layer deposited on another material, such as silicon on sapphire. When reference is made to a substrate assembly, various process steps may have been previously used to form or define regions, junctions, various structures or features, and openings such as transistors, active areas, diffusions, implanted regions, vias, contact openings, high aspect ratio openings, capacitor plates, barriers for capacitors, etc.

"Layer," as used herein, refers to any layer that can be formed on a substrate from one or more precursors and/or reactants according to the deposition process described herein. The term "layer" is meant to include layers specific to the semiconductor industry, such as, but clearly not limited to, a barrier layer, dielectric layer (i.e., a layer having a high dielectric constant), and conductive layer. The term "layer" is synonymous with the term "film" frequently used in the semiconductor industry. The term "layer" is also meant to include layers found in technology outside of semiconductor technology, such as coatings on glass. For example, such layers can be formed directly on fibers, wires, etc., which are substrates other than semiconductor substrates. Further, the layers can be formed directly on the lowest semiconductor surface of the substrate, or they can be formed on any of a variety of layers (e.g., surfaces) as in, for example, a patterned wafer.

The layers or films formed may be in the form of metal-containing films, such as reduced metals, metal silicates, metal oxides, metal nitrides, etc. as well as combinations thereof. For example: a metal oxide layer may include a single metal, the metal oxide layer may include two or more different metals (i.e., it is a mixed metal oxide), or a metal oxide layer may optionally be doped with other metals.

If the metal oxide layer includes two or more different metals, the metal oxide layer can be in the form of alloys, solid solutions, or nanolaminates. Preferably, these have dielectric properties. The metal oxide layer (particularly if it is a dielectric layer) preferably includes one or more of $BaTiO_3$, $SrTiO_3$, $CaTiO_3$, $(Ba,Sr)TiO_3$, $SrTa_2O_6$, $SrBi_2Ta_2O_9$ (SBT), $SrHfO_3$, $SrZrO_3$, $BaHfO_3$, $BaZrO_3$, $(Pb,Ba)Nb_2O_6$, $(Sr,Ba)Nb_2O_6$, $Pb[(Sc,Nb)_{0.575}Ti_{0.425}]O_3$ (PSNT), $La_2O_3$, $Y_2O_3$, $LaAlO_3$, $YAlO_3$, $Pr_2O_3$, $Ba(Li,Nb)_{1/4}O_3$—$PbTiO_3$, and $Ba(0.6)Sr(0.4)TiO_3$—MgO. Surprisingly, the metal oxide layer formed according to the present invention is essentially free of carbon. Preferably metal-oxide layers formed by the systems and methods of the present invention are essentially free of carbon, hydrogen, halides, phosphorus, sulfur, nitrogen or compounds thereof. As used herein, "essentially free" is defined to mean that the metal-containing layer may include a small amount of the above impurities. For example, for metal-oxide layers, "essentially free" means that the above impurities are present in an amount of less than 1 atomic percent, such that they have a minor effect on the chemical properties, mechanical properties, physical form (e.g. crystallinity), or electrical properties of the film.

Various metal-containing compounds can be used in various combinations, optionally with one or more organic solvents (particularly for CVD processes), to form a precursor composition. Advantageously, some of the metal-containing compounds disclosed herein can be used in ALD without adding solvents. "Precursor" and "precursor composition" as used herein, refer to a composition usable for forming, either alone or with other precursor compositions (or reactants), a layer on a substrate assembly in a deposition process. Further, one skilled in the art will recognize that the type and amount of precursor used will depend on the content of a layer which is ultimately to be formed using a vapor deposition process. The preferred precursor compositions of the present invention are preferably liquid at the vaporization temperature and, more preferably, are preferably liquid at room temperature.

The precursor compositions may be liquids or solids at room temperature (preferably, they are liquids at the vaporization temperature). Typically, they are liquids sufficiently volatile to be employed using known vapor deposition techniques. However, as solids they may also be sufficiently volatile that they can be vaporized or sublimed from the solid state using known vapor deposition techniques. If they are less volatile solids, they are preferably sufficiently soluble in an organic solvent or have melting points below their decomposition temperatures such that they can be used in flash vaporization, bubbling, microdroplet formation techniques, etc.

Herein, vaporized metal-containing compounds may be used either alone or optionally with vaporized molecules of other metal-containing compounds or optionally with vaporized solvent molecules or inert gas molecules, if used. As used herein, "liquid" refers to a solution or a neat liquid (a liquid at room temperature or a solid at room temperature that melts at an elevated temperature). As used herein, "solution" does not require complete solubility of the solid but may allow for some undissolved solid, as long as there is a sufficient amount of the solid delivered by the organic solvent into the vapor phase for chemical vapor deposition processing. If solvent dilution is used in deposition, the total molar concentration of solvent vapor generated may also be considered as a inert carrier gas.

"Inert gas" or "non-reactive gas," as used herein, is any gas that is generally unreactive with the components it comes in contact with. For example, inert gases are typically selected from a group including nitrogen, argon, helium, neon, krypton, xenon, any other non-reactive gas, and mixtures thereof. Such inert gases are generally used in one or more purging processes described according to the present invention, and in some embodiments may also be used to assist in precursor vapor transport.

Solvents that are suitable for certain embodiments of the present invention may be one or more of the following: aliphatic hydrocarbons or unsaturated hydrocarbons (C3-C20, and preferably C5-C10, cyclic, branched, or linear), aromatic hydrocarbons (C5-C20, and preferably C5-C10), halogenated hydrocarbons, silylated hydrocarbons such as alkylsilanes, alkylsilicates, ethers, polyethers, thioethers, esters, lactones, nitrites, silicone oils, or compounds containing combinations of any of the above or mixtures of one or more of the above. The compounds are also generally compatible with each other, so that mixtures of variable quantities of the metal-containing compounds will not interact to significantly chance their physical properties.

The precursor compositions of the present invention can, optionally, be vaporized and deposited/chemisorbed substantially simultaneously with, and in the presence of, one or more reaction gases. Alternatively, the metal-containing layers may be formed by alternately introducing the precursor composition and the reaction gas(es) during each deposition cycle. Such reaction gases may typically include oxygen, water vapor, ozone, nitrogen oxides, sulfur oxides, hydrogen, hydrogen sulfide, hydrogen selenide, hydrogen telluride, hydrogen peroxide, ammonia, organic amines, hydrazines (e.g., hydrazine, methylhydrazine, symmetrical and unsymmetrical dimethylhydrazines), silanes, disilanes and higher silanes, diborane, plasma, air, borazene (nitrogen source), carbon monoxide (reductant), alcohols, and any combination of these gases. For example, oxygen-containing sources are typically used for the deposition of metal-oxide layers. Preferable optional reaction gases used in the formation of metal-oxide layers include oxidizing gases (e.g., oxygen, ozone, and nitric oxide).

Suitable substrate materials of the present invention include conductive materials, semiconductive materials, conductive metal-nitrides, conductive metals, conductive metal oxides, etc. The substrate on which the metal-containing layer is formed is preferably a semiconductor substrate or substrate assembly. A wide variety of semiconductor materials are contemplated, such as for example, borophosphosilicate glass (BPSG), silicon such as, e.g., conductively doped polysilicon, monocrystalline silicon, etc. (for this invention, appropriate forms of silicon are simply referred to as "silicon"), for example in the form of a silicon wafer, tetraethylorthosilicate (TEOS) oxide, spin on glass (i.e., a thin layer of $SiO_2$, optionally doped, deposited by a spin on process), TiN, TaN, W, Ru, Al, Cu, noble metals, etc. A substrate assembly may also contain a layer that includes platinum, iridium, iridium oxide, rhodium, ruthenium, ruthenium oxide, strontium ruthenate, lanthanum nickelate, titanium nitride, tantalum nitride, tantalum-silicon-nitride, silicon dioxide, aluminum, gallium arsenide, glass, etc., and other existing or to-be-developed materials used in semiconductor constructions, such as dynamic random access memory (DRAM) devices, static random access memory (SRAM) devices, and ferroelectric memory (FERAM) devices, for example.

For substrates including semiconductor substrates or substrate assemblies, the layers can be formed directly on the lowest semiconductor surface of the substrate, or they can be formed on any of a variety of the layers (i.e., surfaces) as in a patterned wafer, for example.

Substrates other than semiconductor substrates or substrate assemblies can also be used in methods of the present invention. Any substrate that may advantageously form a metal-containing layer thereon, such as a metal oxide layer, may be used, such substrates including, for example, fibers, wires, etc.

A preferred deposition process for the present invention is a vapor deposition process. Vapor deposition processes are generally favored in the semiconductor industry due to the process capability to quickly provide highly conformal layers even within deep contacts and other openings.

The precursor compositions can be vaporized in the presence of an inert carrier gas if desired. Additionally, an inert carrier gas can be used in purging steps in an ALD process (discussed below). The inert carrier gas is typically one or more of nitrogen, helium, argon, etc. In the context of the present invention, an inert carrier gas is one that does not interfere with the formation of the metal-containing layer. Whether done in the presence of a inert carrier gas or not, the vaporization is preferably done in the absence of oxygen to avoid oxygen contamination of the layer (e.g., oxidation of silicon to form silicon dioxide or oxidation of precursor in the vapor phase prior to entry into the deposition chamber).

Chemical vapor deposition (CVD) and atomic layer deposition (ALD) are two vapor deposition processes often employed to form thin, continuous, uniform, metal-containing layers onto semiconductor substrates. Using either vapor deposition process, typically one or more precursor compositions are vaporized in a deposition chamber and optionally combined with one or more reaction gases and directed to and/or contacted with the substrate to form a metal-containing layer on the substrate. It will be readily apparent to one skilled in the art that the vapor deposition process may be enhanced by employing various related techniques such as plasma assistance, photo assistance, laser assistance, as well as other techniques.

Chemical vapor deposition (CVD) has been extensively used for the preparation of metal-containing layers, such as dielectric layers, in semiconductor processing because of its ability to provide conformal and high quality dielectric layers at relatively fast processing times. Typically, the desired precursor compositions are vaporized and then introduced into a deposition chamber containing a heated substrate with optional reaction gases and/or inert carrier gases in a single deposition cycle. In a typical CVD process, vaporized precursors are contacted with reaction gas(es) at the substrate surface to form a layer (e.g., dielectric layer). The single deposition cycle is allowed to continue until the desired thickness of the layer is achieved.

Typical CVD processes generally employ precursor compositions in vaporization chambers that are separated from the process chamber wherein the deposition surface or wafer is located. For example, liquid precursor compositions are typically placed in bubblers and heated to a temperature at which they vaporize, and the vaporized liquid precursor composition is then transported by an inert carrier gas passing over the bubbler or through the liquid precursor composition. The vapors are then swept through a gas line to the deposition chamber for depositing a layer on substrate surface(s) therein. Many techniques have been developed to precisely control this process. For example, the amount of precursor composition transported to the deposition chamber can be precisely controlled by the temperature of the reservoir containing the precursor composition and by the flow of an inert carrier gas bubbled through or passed over the reservoir.

A typical CVD process may be carried out in a chemical vapor deposition reactor, such as a deposition chamber available under the trade designation of 7000 from Genus, Inc. (Sunnyvale, Calif.): a deposition chamber available under the trade designation of 5000 from Applied Materials, Inc. (Santa Clara, Calif.), or a deposition chamber available under the trade designation of Prism from Novelus, Inc. (San Jose, Calif.). However, any deposition chamber suitable for performing CVD may be used.

Several modifications of the CVD process and chambers are possible, for example, using atmospheric pressure chemical vapor deposition, low pressure chemical vapor deposition (LPCVD), plasma enhanced chemical vapor deposition (PECVD), hot wall or cold wall reactors or any other chemical vapor deposition technique. Furthermore, pulsed CVD can be used, which is similar to ALD (discussed in greater detail below) but does not rigorously avoid intermixing of precursor and reactant gas streams. Also, for pulsed CVD, the deposition thickness is dependent on the exposure time, as opposed to ALD, which is self-limiting (discussed in more detail below).

Alternatively, and preferably, the vapor deposition process employed in the methods of the present invention is a multi-cycle atomic layer deposition (ALD) process. Such a process is advantageous, in particular advantageous over a CVD process, in that it provides for improved control of atomic-level thickness and uniformity to the deposited layer (e.g., dielectric layer) by providing a plurality of deposition cycles. The self-limiting nature of ALD provides a method of depositing a film on a wide variety of reactive surfaces including, for example, surfaces with irregular topographies, with better step coverage than is available with CVD or other "line of sight" deposition methods (e.g., evaporation and physical vapor deposition, i.e., PVD or sputtering). Further, ALD processes typically expose the metal-containing compounds to lower volatilization and reaction temperatures, which tends to decrease degradation of the precursor as compared to, for example, typical CVD processes. See, for example, U.S. Pat. No. 7,416,994 (Quick).

Generally, in an ALD process each reactant is pulsed sequentially onto a suitable substrate, typically at deposition temperatures of at least 25° C., preferably at least 150° C., and more preferably at least 200° C. Typical ALD deposition temperatures are no greater than 400° C., preferably no greater than 350° C., and even more preferably no greater than 250° C. These temperatures are generally lower than those presently used in CVD processes, which typically include deposition temperatures at the substrate surface of at least 150° C., preferably at least 200° C.; and more preferably at least 250° C. Typical CVD deposition temperatures are no greater than 600° C., preferably no greater than 500° C., and even more preferably no greater than 400° C.

Under such conditions the film growth by ALD is typically self-limiting (i.e., when the reactive sites on a surface are used up in an ALD process, the deposition generally stops), insuring not only excellent conformality but also good large area uniformity plus simple and accurate composition and thickness control. Due to alternate dosing of the precursor compositions and/or reaction gases, detrimental vapor-phase reactions are inherently eliminated, in contrast to the CVD process that is carried out by continuous co-reaction of the precursors and/or reaction gases. (See Vehkamälki et al, "Growth of $SrTiO_3$ and $BaTiO_3$ Thin Films by Atomic Layer Deposition," Electrochemical and Solid-State Letters, 2(10): 504-506 (1999)).

A typical ALD process includes exposing a substrate (which may optionally be pretreated with, for example, water and/or ozone) to a first chemical to accomplish chemisorption of the species onto the substrate. The term "chemisorption" as used herein refers to the chemical adsorption of vaporized reactive metal-containing compounds on the surface of a substrate. The adsorbed species are typically irreversibly bound to the substrate surface as a result of relatively strong binding forces characterized by high adsorption energies (e.g., >30 kcal/mol), comparable in strength to ordinary chemical bonds. The chemisorbed species typically form a monolayer on the substrate surface. (See "The Condensed Chemical Dictionary", 10th edition, revised by G. G. Hawley, published by Van Nostrand Reinhold Co. New York, 225 (1981)). The technique of ALD is based on the principle of the formation of a saturated monolayer of reactive precursor molecules by chemisorption. In ALD one or more appropriate precursor compositions or reaction gases are alternately introduced (e.g., pulsed) into a deposition chamber and chemisorbed onto the surfaces of a substrate. Each sequential introduction of a reactive compound (e.g., one or more precursor compositions and one or more reaction gases) is typically separated by an inert carrier gas purge. Each precursor composition co-reaction adds a new atomic layer to previously deposited layers to form a cumulative solid layer. The cycle is repeated to gradually form the desired layer thickness. It should be understood that ALD can alternately utilize one precursor composition, which is chemisorbed, and one reaction gas, which reacts with the chemisorbed species.

Practically, chemisorption might not occur on all portions of the deposition surface (e.g., previously deposited ALD material). Nevertheless, such imperfect monolayer is still considered a monolayer in the context of the present invention. In many applications, merely a substantially saturated monolayer may be suitable. A substantially saturated monolayer is one that will still yield a deposited monolayer or less of material exhibiting the desired quality and/or properties.

A typical ALD process includes exposing an initial substrate to a first chemical species A (e.g., a metal-containing compound as described herein) to accomplish chemisorption of the species onto the substrate. Species A can react either with the substrate surface or with Species B (described below) but not with itself. Typically in chemisorption, one or more of the ligands of Species A is displaced by reactive groups on the substrate surface. Theoretically, the chemisorption forms a monolayer that is uniformly one atom or molecule thick on the entire exposed initial substrate, the monolayer being composed of Species A, less any displaced ligands. In other words, a saturated monolayer is substantially formed on the substrate surface. Practically, chemisorption may not occur on all portions of the substrate. Nevertheless, such a partial monolayer is still understood to be a monolayer in the context of the present invention. In many applications, merely a substantially saturated monolayer may be suitable. In one aspect, a substantially saturated monolayer is one that will still yield a deposited monolayer or less of material exhibiting the desired quality and/or properties. In another aspect, a substantially saturated monolayer is one that is self-limited to further reaction with precursor.

The first species (e.g., substantially all non-chemisorbed molecules of Species A) as well as displaced ligands are purged from over the substrate and a second chemical species, Species B (e.g., a different metal-containing compound or reactant gas) is provided to react with the monolayer of Species A. Species B typically displaces the remaining ligands from the Species A monolayer and thereby is chemisorbed and forms a second monolayer. This second monolayer displays a surface which is reactive only to Species A. Non-chemisorbed Species B, as well as displaced ligands and other byproducts of the reaction are then purged and the steps are repeated with exposure of the Species B monolayer to vaporized Species A. Optionally, the second species can react with the first species, but not chemisorb additional material thereto. That is, the second species can cleave some portion of the chemisorbed first species, altering such monolayer without forming another monolayer thereon, but leaving reactive sites available for formation of subsequent monolayers. In other ALD processes, a third species or more may be successively chemisorbed (or reacted) and purged just as described for the first and second species, with the understanding that each introduced species reacts with the monolayer produced immediately prior to its introduction. Optionally, the second species (or third or subsequent) can include at least one reaction gas if desired.

Thus, the use of ALD provides the ability to improve the control of thickness, composition, and uniformity of metal-containing layers on a substrate. For example, depositing thin layers of metal-containing compound in a plurality of cycles provides a more accurate control of ultimate film thickness. This is particularly advantageous when the precursor composition is directed to the substrate and allowed to chemisorb thereon, preferably further including at least one reaction gas that reacts with the chemisorbed species on the substrate, and even more preferably wherein this cycle is repeated at least once.

Purging of excess vapor of each species following deposition/chemisorption onto a substrate may involve a variety of techniques including, but not limited to, contacting the substrate and/or monolayer with an inert carrier gas and/or lowering pressure to below the deposition pressure to reduce the concentration of a species contacting the substrate and/or chemisorbed species. Examples of carrier gases, as discussed above, may include $N_2$, Ar, He, etc. Additionally, purging may instead include contacting the substrate and/or monolayer with any substance that allows chemisorption by-products to desorb and reduces the concentration of a contacting species preparatory to introducing another species. The contacting species may be reduced to some suitable concentration or partial pressure known to those skilled in the art based on the specifications for the product of a particular deposition process.

ALD is often described as a self-limiting process, in that a finite number of sites exist on a substrate to which the first species may form chemical bonds. The second species might only react with the surface created from the chemisorption of the first species and thus, may also be self-limiting. Once all of the finite number of sites on a substrate are bonded with a first species, the first species will not bond to other of the first species already bonded with the substrate. However, process conditions can be varied in ALD to promote such bonding and render ALD not self-limiting, e.g., more like pulsed CVD. Accordingly, ALD may also encompass a species forming other than one monolayer at a time by stacking of a species, forming a layer more than one atom or molecule thick.

The described method indicates the "substantial absence" of the second precursor (i.e., second species) during chemisorption of the first precursor since insignificant amounts of the second precursor might be present. According to the knowledge and the preferences of those with ordinary skill in the alt, a determination can be made as to the tolerable amount of second precursor and process conditions selected to achieve the substantial absence of the second precursor.

Thus, during the ALD process, numerous consecutive deposition cycles are conducted in the deposition chamber, each cycle depositing a very thin metal-containing layer (usually less than one monolayer such that the growth rate on average is 0.2 to 3.0 Angstroms per cycle), until a layer of the desired thickness is built up on the substrate of interest. The layer deposition is accomplished by alternately introducing (i.e., by pulsing) precursor composition(s) into the deposition chamber containing a substrate, chemisorbing the precursor composition(s) as a monolayer onto the substrate surfaces, purging the deposition chamber, then introducing to the chemisorbed precursor composition(s) reaction gases and/or other precursor composition(s) in a plurality of deposition cycles until the desired thickness of the metal-containing layer is achieved. Preferred thicknesses of the metal-containing layers of the present invention are at least 1 angstrom (Å), more preferably at least 5 Å, and more preferably at least 10 Å. Additionally, preferred film thicknesses are typically no greater than 500 Å, more preferably no greater than 400 Å, and more preferably no greater than 300 Å.

The pulse duration of precursor composition(s) and inert carrier gas(es) is generally of a duration sufficient to saturate the substrate surface. Typically, the pulse duration is at least 0.1, preferably at least 0.2 second, and more preferably at least 0.5 second. Preferred pulse durations are generally no greater than 5 seconds, and preferably no greater than 3 seconds.

In comparison to the predominantly thermally driven CVD, ALD is predominantly chemically driven. Thus, ALD may advantageously be conducted at much lower temperatures than CVD. During the ALD process, the substrate temperature may be maintained at a temperature sufficiently low to maintain intact bonds between the chemisorbed precursor composition(s) and the underlying substrate surface and to prevent decomposition of the precursor composition(s). The temperature, on the other hand, must be sufficiently high to avoid condensation of the precursor composition(s). Typically the substrate is kept at a temperature of at least 25° C., preferably at least 150° C., and more preferably at least 200° C. Typically the substrate is kept at a temperature of no greater than 400° C., preferably no greater than 300° C., and more preferably no greater than 250° C., which, as discussed above, is generally lower than temperatures presently used in typical CVD processes. Thus, the first species or precursor composition is chemisorbed at this temperature. Surface reaction of the second species or precursor composition can occur at substantially the same temperature as chemisorption of the first precursor or, optionally but less preferably, at a substantially different temperature. Clearly, some small variation in temperature, as judged by those of ordinary skill, can occur but still be considered substantially the same temperature by providing a reaction rate statistically the same as would occur at the temperature of the first precursor chemisorption. Alternatively, chemisorption and subsequent reactions could instead occur at substantially exactly the same temperature.

For a typical vapor deposition process, the pressure inside the deposition chamber is at least $10^{-8}$ torr ($1.3 \times 10^{-6}$ Pa), preferably at least $10^{-7}$ torr ($1.3 \times 10^{-5}$ Pa), and more preferably at least $10^{-6}$ torr ($1.3 \times 10^{-4}$ Pa). Further, deposition pressures are typically no greater than 10 torr ($1.3 \times 10^{3}$ Pa), preferably no greater than 1 torr ($1.3 \times 10^{2}$ Pa), and more preferably no greater than $10^{-1}$ torr (13 Pa). Typically, the deposition chamber is purged with an inert carrier gas after the vaporized precursor composition(s) have been introduced into the chamber and/or reacted for each cycle. The inert carrier gas/gases can also be introduced with the vaporized precursor composition(s) during each cycle.

The reactivity of a precursor composition can significantly influence the process parameters in ALD. Under typical CVD process conditions, a highly reactive compound may react in the gas phase generating particulates, depositing prematurely on undesired surfaces, producing poor films, and/or yielding poor step coverage or otherwise yielding non-uniform deposition. For at least such reason, a highly reactive compound might be considered not suitable for CVD. However, some compounds not suitable for CVD are superior ALD precursors. For example, if the first precursor is gas phase reactive with the second precursor, such a combination of compounds might not be suitable for CVD, although they could be used in ALD. In the CVD context, concern might also exist regarding sticking coefficients and surface mobility, as known to those skilled in the art, when using highly gas-phase reactive precursors, however, little or no such concern would exist in the ALD context.

After layer formation on the substrate, an annealing process may be optionally performed in situ in the deposition chamber in a reducing, inert, plasma, or oxidizing atmosphere. Preferably, the annealing temperature is at least 400° C., more preferably at least 600° C. The annealing temperature is preferably no greater than 1000° C., more preferably no greater than 750° C. and even more preferably no greater than 700° C.

The annealing operation is preferably performed for a time period of at least 0.5 minute, more preferably for a time period of at least 1 minute. Additionally, the annealing operation is preferably performed for a time period of no greater than 60 minutes, and more preferably for a time period of no greater than 10 minutes.

One skilled in the art will recognize that such temperatures and time periods may vary. For example, furnace anneals and rapid thermal annealing may be used, and further, such anneals may be performed in one or more annealing steps.

As stated above, the use of the compounds and methods of forming films of the present invention are beneficial for a wide variety of thin film applications in semiconductor structures, particularly those using high dielectric materials. For example, such applications include gate dielectrics and capacitors such as planar cells, trench cells (e.g., double sidewall trench capacitors), stacked cells (e.g., crown, V-cell, delta cell, multi-fingered, or cylindrical container stacked capacitors), as well as field effect transistor devices.

A system that can be used to perform vapor deposition processes (chemical vapor deposition or atomic layer deposition) of the present invention is shown in FIG. 1. The system includes an enclosed vapor deposition chamber 10, in which a vacuum may be created using turbo pump 12 and backing pump 14. One or more substrates 16 (e.g., semiconductor substrates or substrate assemblies) are positioned in chamber 10. A constant nominal temperature is established for substrate 16, which can vary depending on the process used. Substrate 16 may be heated, for example, by an electrical resistance heater 18 on which substrate 16 is mounted. Other known methods of heating the substrate may also be utilized.

In this process, precursor compositions as described herein, 60 and/or 61, are stored in vessels 62. The precursor composition(s) are vaporized and separately fed along lines 64 and 66 to the deposition chamber 10 using, for example, an inert carrier gas 68. A reaction gas 70 may be supplied along line 72 as needed. Also, a purge gas 74, which is often the same as the inert carrier gas 68, may be supplied along line 76 as needed. As shown, a series of valves 80-85 are opened and closed as required.

The following examples are offered to further illustrate various specific embodiments and techniques of the present invention. It should be understood, however, that many variations and modifications understood by those of ordinary skill in the art may be made while remaining within the scope of the present invention. Therefore, the scope of the invention is not intended to be limited by the following example. Unless specified otherwise, all percentages shown in the examples are percentages by weight.

EXAMPLES

Example 1

Synthesis and Characterization of a Ligand Source of Formula III, with $R^1$=tert-butyl; $R^5$=isopropyl; $R^2$=$R^4$=methyl; and $R^3$=H: N-isopropyl-(4-tert-butylimino)-2-penten-2-amine An oven-dry 1-L Schlenk flask was charged with 38.0 g of triethyloxonium tetrafluoroborate (0.2 mol) and 75 mL diethyl ether under argon atmosphere, and fitted with an addition funnel. 250 mL of dichloromethane and 28.2 grains of N-isopropyl-4-amino-3-penten-2-one (0.2 mol) were charged into the addition funnel and this solution was added dropwise, then stirred for 30 minutes. A solution of 21 mL tert-butyl amine (0.2 mol) and 25 mL dichloromethane was charged into the addition funnel and added to the reaction solution, which was then stirred overnight. Volatiles were then removed in vacuo and the resulting yellow-orange solid was washed with two 100 mL aliquots of cold ethyl acetate while the flask was placed in an ice-bath. After decanting off each ethyl acetate wash, the yellow solid residue was added to a mixture of 500 mL benzene and 500 mL water containing 8.0 g sodium hydroxide (0.2 mol). The mixture was stirred for three minutes, then the organic phase was separated. The aqueous phase was extracted three times, each with 100 mL diethyl ether portions. All the organic phases were combined, dried over sodium sulfate and concentrated on a rotary evaporator. The crude product was then distilled through a 20 cm glass-bead packed column and short path still head. The desired product was collected in 96% pure form at 34-42° C., 40 mTorr (5.3 Pa) pressure. The only impurity observed by gas chromatography-mass spectrometry (GCMS) was N-isopropyl-(4-isopropylimino)-2-penten-2-amine. The amount of N-isopropyl-(4-isopropylimino)-2-penten-2-amine formed may be limited by limiting the reaction time (e.g., 30 minutes after addition of the tert-butyl amine). Allowing the reaction to stir overnight may result in the formation of more N-isopropyl-(4-isopropylimino)-2-penten-2-amine.

Example 2

Synthesis and Characterization of a Metal-Containing Compound of Formula I, with M=Sr (n=2); $R^1$=tert-butyl; $R^5$=isopropyl; $R^2$=$R^4$=methyl; $R^3$=H; x=2; and z=0: Strontium bis(N-isopropyl-(4-tert-butylamino)-2-penten-2-aminato)

In a dry box, a 500 mL Schlenk flask was charged with 13.819 g of strontium bis(hexamethyldisilazane)bis(tetrahydrofuran) (25 mmol) and 100 mL toluene. A second Schlenk flask was charged with 9.800 g of N-isopropyl-(4-tert-butylimino)-2-penten-2-amine (50 mmol) and 100 mL toluene. The ligand solution was added to the strontium solution, immediately producing a bright yellow reaction solution, which was stirred for 60 hours. Volatiles were then removed in vacuo. The crude product, a bright yellow solid, was charged into a sublimator in dry box. The sublimator was attached to a vacuum manifold in a fume hood, evacuated to less than 100 mTorr (13 Pa) and heated to 115° C. A total of 8.204 g of off-white crystalline solid was sublimed in three batches (68.5% yield). Elemental Analysis calculated for $C_{24}H_{46}N_4Sr$: Sr, 18.3%. Found 18.5%. $^1H$ nuclear magnetic resonance (NMR) ($C_6D_6$, 25° C., δ) 4.234 (s, 2H, β-CH), 3.586 (septet, J=6.0 Hz, 2H, $CH(CH_3)_2$), 1.989 (s, 6H, α-C—$CH_3$ (isopropyl side)), 1.907 (s, 6H, α-C—$CH_3$ (tert-butyl side)), 1.305 (s, 18H, $C(CH_3)_3$), 1.200 (d, J=6.0 Hz, 12H, $CH(CH_3)_2$); $^{13}C\{^1H\}$ ($C_6D_6$, 25° C., δ) 161.19 (s, α-C—$CH_3$ (isopropyl side)), 160.44 (s, α-C—$CH_3$ (tert-butyl side)), 88.33 (s, β-CH), 54.07 (s, $C(CH_3)_3$), 49.86 (s, $CH(CH_3)_2$)), 32.44 (s, $C(CH_3)_3$), 26.50 (s, $CH(CH_3)_2$), 24.84 (s, α-C—$CH_3$ (tert-butyl side)), 22.09 (s, α-C—$CH_3$ (isopropyl side)).

Example 3

Synthesis and Characterization of a Metal-containing Compound of Formula II, with M=Sr (n=2); $R^1$=$R^5$=tert-butyl; $R^6$=$R^{10}$=isopropyl; $R^2$=$R^4$=$R^7$=$R^9$=methyl; $R^3$=$R^8$=H; and z=0: Strontium (N-isopropyl-(4-isopropylimino)-2-penten-2-aminato)(N-tert-butyl-(4-tert-butylimino)-2-penten-2-aminato)

In a dry box, a 500 mL Schlenk flask was charged with 5.526 g of strontium bis(hexamethyldisilazane) (10 mmol) and 100 mL toluene. A solution of 2.104 g N-tert-butyl-(4-tert-butylimino)-2-penten-2-amine (10 mmol, prepared according to literature) in 20 mL toluene was added to the reaction flask. The reaction solution was stirred for 18 hours. A solution of 1.823 g N-isopropyl-(4-isopropylimino)-2-penten-2-amine (10 mmol, prepared according to literature) in 20 mL toluene was added to the reaction flask. The reaction solution was then stirred an additional 24 hours. Volatiles were removed in vacuo to afford a red-brown solid, which was charged into a sublimator in a dry box (4.70 g, 9.98 mmol). The sublimator was evacuated on a vacuum manifold in a hood and heated. At around 80° C., the pot residue appeared to begin to melt and bump. A yellow-brown condensate was collected on the cold finger while heating the pot at 112° C. at 115 mTorr (15.3 Pa). 2.856 g of a yellow semi-crystalline but somewhat oily solid was recovered from the cold-finger (59.7% yield). Analysis by proton NMR indicates that the sublimed material consists of a 1:1:1 mixture of the title compound with Strontium bis(N-isopropyl-(4-isopropyl imino)-2-penten-2-aminato) and Strontium bis(N-tert-butyl-(4-tert-butylimino)-2-penten-2-aminato). The material also contains a 0.3 relative ratio of N-tert-butyl-(4-tert-butylimino)-2-penten-2-amine. The chemical shifts for the title compound are as follows: $^1H$ NMR($C_6D_6$, 25° C., δ) 4.218 (s, 2H, β-CH), 3.586 (septet, J=6.0 Hz, 2H, $CH(CH_3)_2$), 1.990 (s, 6H, α-C—$CH_3$ (tert-butyl)), 1.865 (s, 6H. α-C—$CH_3$ (isopropyl)), 1.325 (s, 18H, $C(CH_3)_3$), 1.172 (d, J=6.0 Hz, 12H, $CH(CH_3)_2$); $^{13}C\{^1H\}$ ($C_6D_6$, 25° C., δ) 160.95 (s, α-C—$CH_3$ (isopropyl)), 160.79 (s, α-C—$CH_3$ (tert-butyl))-90.05 (s, β-CH (tert-butyl)), 86.51 (s, β-CH (isopropyl)), 53.99 (s, $C(CH_3)_3$), 49.93 (s, $CH(CH_3)_2$)), 32.81 (s, C $(CH_3)_3$), 25.06 (s, $CH(CH_3)_2$), 24.83 (s, α-C—$CH_3$ (tert-butyl)), 22.05 (s, α-C—$CH_3$ (isopropyl)). Elemental Analysis calculated for $C_{24}H_{46}N_4Sr$: Sr, 18.3%. Found 17.5%.

Example 4

Alternate Synthesis of the Metal-Containing Compound Prepared and Characterized in Example 3 by Ligand Exchange Reactions Between Metal-Containing Compounds Including Different Symmetrical β-Diketiminate Ligands A 50 mL schlenk flask was charged with 0.50 g of bis(N-tert-butyl-(4-tert-butylimino)-2-penten-2-aminato)strontium (1 mmol), 0.45 g of bis(N-isopropyl-(4-isopropylimino)-2-penten-2-aminato)strontium (1 mmol), and 20 mL toluene. The resulting solution was refluxed for 24 hours, then volatiles were removed in vacuo. A sample of the resulting yellow solid was submitted for proton NMR analysis, and the results indicated approximately a 1:1:1 mixture of bis(N-tert-butyl-(4-tert-butylimino)-2-penten-2-aminato)strontium:bis(N-isopropyl-(4-isopropylimino)-2-penten-2-aminato)strontium: (N-isopropyl-(4-isopropylimino)-2-penten-2-aminato) (N-tert-butyl-(4-tert-butylimino)-2-penten-2-aminato) strontium, with approximately a 0.3 ratio of free N-tert-butyl-(4-tert-butylimino)-2-penten-2-amine.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A vapor deposition method comprising: contacting a vapor with a substrate using a vapor deposition process, the vapor comprising at least one compound of the formula (Formula I):

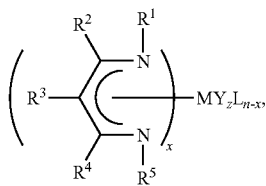

wherein:
M is selected from the group consisting of a Group 2 metal, yttrium, a Lanthanide, and combinations thereof;
each L is independently an anionic ligand;
each Y is independently a neutral ligand;
n represents the valence state of the metal;
z is from 0 to 10;
x is from 1 to n; and
each $R^1$, $R^2$, $R^3$, $R^4$, and $R^5$ is independently hydrogen or an organic group;
with the proviso that one or more of the following apply: $R^1$ different than $R^5$, or $R^2$ is different than $R^4$.

2. The method of claim 1 wherein the method forms a metal-containing material on at least one surface of the substrate.

3. The method of claim 1 wherein each $R^1$, $R^2$, $R^3$, $R^4$, and $R^5$ is independently hydrogen or an organic group having 1 to 10 carbon atoms.

4. The method of claim 3 wherein $R^1$=isopropyl; and $R^5$=tert-butyl.

5. The method of claim 3 wherein $R^2$=$R^4$=methyl; and $R^3$=H.

6. The method of claim 1 wherein at least one L is selected from the group consisting of a halide, an alkoxide group, an amide group, a mercaptide group, cyanide, an alkyl group, an amidinate group, a guanidinate group, an isoureate group, a β-diketonate group, a β-iminoketonate group, a β-diketiminate group, and combinations thereof.

7. The method of claim 1 wherein at least one Y is selected from the group consisting of a carbonyl, a nitrosyl, ammonia, an amine, nitrogen, a phosphine, an alcohol, water, tetrahydrofuran, and combinations thereof.

8. A vapor deposition method comprising: directing a vapor to a semiconductor substrate or substrate assembly using a vapor deposition process, the vapor comprising at least one compound of the formula (Formula I):

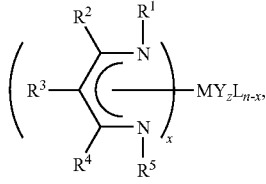

wherein:
M is selected from the group consisting of a Group 2 metal, yttrium, a Lanthanide, and combinations thereof;
each L is independently an anionic ligand;
each Y is independently a neutral ligand;
n represents the valence state of the metal;
z is from 0 to 10;
x is from 1 to n; and
each $R^1$, $R^2$, $R^3$, $R^4$, and $R^5$ is independently hydrogen or an organic group;
with the proviso that one or more of the following apply: $R^1$ is different than $R^5$, or $R^2$ is different than $R^4$.

9. The method of claim 8 wherein the method forms a metal-containing material on at least one surface of the semiconductor substrate or substrate assembly.

10. The method of claim 8 further comprising providing at least one reaction gas.

11. The method of claim 8 wherein the vapor deposition process is a chemical vapor deposition process.

12. The method of claim 8 wherein the vapor deposition process is an atomic layer deposition process comprising a plurality of deposition cycles.

13. A vapor deposition method comprising:
directing a first vapor to a semiconductor substrate or substrate assembly using a vapor deposition process, the first vapor comprising at least one compound of the formula (Formula I):

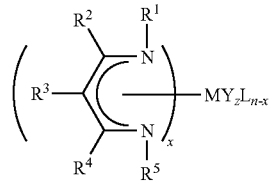

wherein:
M is selected from the group consisting of a Group 2 metal, yttrium, a Lanthanide, and combinations thereof;
each L is independently an anionic ligand;
each Y is independently a neutral ligand;
n represents the valence state of the metal;
z is from 0 to 10;
x is from 1 to n; and
each $R^1$, $R^2$, $R^3$, $R^4$, and $R^5$ is independently hydrogen or an organic group;
with the proviso that one or more of the following apply: $R^1$ is different than $R^5$, or $R^2$ is different than $R^4$; and
directing a second vapor comprising at least one metal-containing compound different than Formula I to the semiconductor substrate or substrate assembly using a vapor deposition process.

14. The method of claim 13 wherein the method forms a metal-containing material on at least one surface of the semiconductor substrate or substrate assembly.

15. The method of claim 13 wherein the metal of the at least one metal-containing compound different than Formula I is selected from the group consisting of Ti, Ta, Bi, Hf, Zr, Pb, Nb, Mg, Al, and combinations thereof.

16. A vapor deposition method comprising: contacting a vapor with a substrate using a vapor deposition process, the vapor comprising at least one compound of the formula (Formula II):

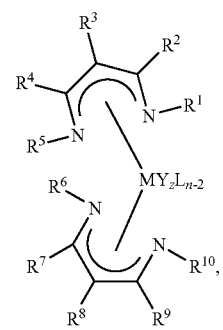

wherein:
M is selected from the group consisting of a Group 2 metal, a Group 3 metal, a Lanthanide, and combinations thereof;
each L is independently an anionic ligand;
each Y is independently a neutral ligand;
n represents the valence state of the metal;
z is from 0 to 10;
each $R^1$, $R^2$, $R^3$, $R^4$, $R^5$, $R^6$, $R^7$, $R^8$, $R^9$, and $R^{10}$ is independently hydrogen or an organic group;
$R^1=R^5$, $R^2=R^4$, $R^6=R^{10}$, and $R^7=R^9$; and
the two β-diketiminate ligands shown in Formula II have different structures.

17. The method of claim 16 wherein the method forms a metal-containing material on at least one surface of the substrate.

18. The method of claim 16 wherein each $R^1$, $R^2$, $R^3$, $R^4$, $R^5$, $R^6$, $R^7$, $R^8$, $R^9$, and $R^{10}$ is independently hydrogen or an organic group having 1 to 10 carbon atoms.

19. The method of claim 18 wherein $R^1=R^5=$tert-butyl; and $R^6=R^{10}=$isopropyl.

20. The method of claim 18 wherein $R^2=R^4=R^7=R^9=$methyl; and $R^3=R^8=$H.

21. The method of claim 20 wherein $R^1=R^5=$tert-butyl; and $R^6=R^{10}=$isopropyl.

22. A vapor deposition method comprising: directing a vapor to a semiconductor substrate or substrate assembly using a vapor deposition process, the vapor comprising at least one compound of the formula (Formula II):

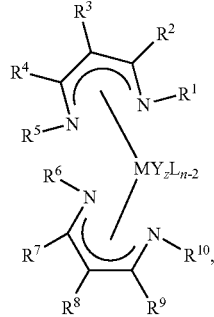

wherein:
M is selected from the group consisting of a Group 2 metal, a Group 3 metal, a Lanthanide, and combinations thereof;
each L is independently an anionic ligand;
each Y is independently a neutral ligand;
n represents the valence state of the metal;
z is from 0 to 10;
each $R^1$, $R^2$, $R^3$, $R^4$, $R^5$, $R^6$, $R^7$, $R^8$, $R^9$, and $R^{10}$ is independently hydrogen or an organic group;
R1=R5, R2=R4, R6=R10, and R7=R9; and
the two β-diketiminate ligands shown in Formula II have different structures.

23. The method of claim 22 wherein the method forms a metal-containing material on at least one surface of the semiconductor substrate or substrate assembly.

24. The method of claim 22 further comprising providing a vapor comprising at least one metal-containing compound different than Formula II, and directing the vapor comprising the at least one metal-containing compound different than Formula II to the semiconductor substrate or substrate assembly.

25. The method of claim 24 wherein the metal of the at least one metal-containing compound different than Formula II is selected from the group consisting of Ti, Ta, Bi, Hf, Zr, Pb, Nb, Mg, Al, and combinations thereof.

* * * * *

UNITED STATES PATENT AND TRADEMARK OFFICE
CERTIFICATE OF CORRECTION

PATENT NO. : 7,858,523 B2
APPLICATION NO. : 12/500738
DATED : December 28, 2010
INVENTOR(S) : Dan Millward et al.

It is certified that error appears in the above-identified patent and that said Letters Patent is hereby corrected as shown below:

In column 1, line 9, delete "(pending)," and insert -- now U.S. Pat. No. 7,572,731, --, therefor.

In column 25, line 21, in Claim 1, after "$R^1$" insert -- is --.

In column 25, line 31, in Claim 5, delete " $R^2=R^4$ " and insert -- $R^2=R^4$ --, therefor.

In column 25, line 32, in Claim 5, delete " $R^3=H.$ " and insert -- $R^3=H.$ --, therefor.

In column 26, lines 16-24, in Claim 13, after " 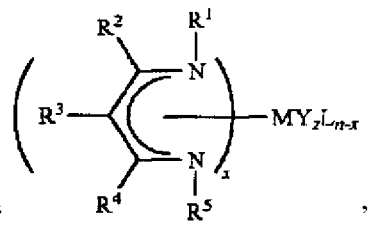 " insert -- , --.

In column 27, line 11, in Claim 16, delete " $R^1=R^5$, $R^2=R^4$, $R^6=R^{10}$, and $R^7=R^9$ ;" and insert -- $R^1=R^5$, $R^2=R^4$, $R^6=R^{10}$, and $R^7=R^9$; --, therefor.

In column 27, line 20, in Claim 19, delete " $R^1=R^5$ " and insert -- $R^1=R^5$ --, therefor.

In column 27, line 21, in Claim 19, delete " $R^6=R^{10}$ " and insert -- $R^6=R^{10}$ --, therefor.

In column 27, line 23, in Claim 20, delete " $R^2=R^4=R^7=R^9$ " and insert -- $R^2=R^4=R^7=R^9$ --, therefor.

In column 27, line 23, in Claim 20, delete " $R^3=R^8=H.$ " and insert -- $R^3=R^8=H.$ --, therefor.

In column 27, line 24, in Claim 21, delete " $R^1=R^5$ " and insert -- $R^1=R^5$ --, therefor.

Signed and Sealed this
Twenty-second Day of February, 2011

David J. Kappos
*Director of the United States Patent and Trademark Office*

CERTIFICATE OF CORRECTION (continued)
U.S. Pat. No. 7,858,523 B2

In column 27, line 25, in Claim 21, delete "$R^6=R^{10}$" and insert -- $R^6=R^{10}$ --, therefor.

In column 28, line 15, in Claim 22, delete "R1=R5, R2=R4, R6=R10, and R7=R9;" and insert -- $R^1=R^5$, $R^2=R^4$, $R^6=R^{10}$, and $R^7=R^9$; --, therefor.